United States Patent [19]

Bonnaffé et al.

[11] Patent Number: 5,262,525
[45] Date of Patent: Nov. 16, 1993

[54] METHOD FOR THE CHEMICAL MODIFICATION OF PROTEINS

[75] Inventors: David Bonnaffé, Paris; André Lubineau, Dourdan; Jean-Louis Séris, Jurancon; Michel Thérisod, Antony, all of France

[73] Assignee: Societe Nationale Elf Aquitaine, Courbevoie, France

[21] Appl. No.: 853,954

[22] Filed: Mar. 19, 1992

[30] Foreign Application Priority Data

Mar. 19, 1991 [FR] France ............... 91 03325

[51] Int. Cl.$^5$ .................................. C07K 3/04
[52] U.S. Cl. ........................ 530/411; 530/410; 530/363
[58] Field of Search ............... 530/410, 411, 363, 406, 530/391.9

[56] References Cited

U.S. PATENT DOCUMENTS

| | | | |
|---|---|---|---|
| 2,865,931 | 12/1958 | Mack et al. | 549/240 |
| 3,433,576 | 3/1969 | Tesoro | 530/410 |
| 4,168,262 | 9/1979 | Kinsella et al. | 530/420 |
| 4,185,090 | 1/1980 | McIntire | 530/359 |
| 4,487,715 | 12/1984 | Nitecki et al. | 530/342 |

FOREIGN PATENT DOCUMENTS 0159637 10/1985 European Pat. Off.
1032363 6/1966 United Kingdom.

OTHER PUBLICATIONS

Morrison and Boyd, Organic Chemistry, Third Edition, Allywand Bacon, pp. 876-877.
Wang et al., in Journal of Parenteral Science and Technology, Sep. 1988, vol. 42, No. 2S, pp. 53-526.

*Primary Examiner*—Michael G. Wityshyn
*Assistant Examiner*—C. Sayala
*Attorney, Agent, or Firm*—Burgess, Ryan & Wayne

[57] ABSTRACT

Method for the chemical modification of proteins using a reagent of general formula

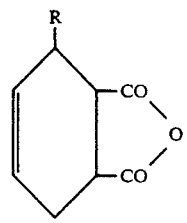

(I)

obtained from the diene

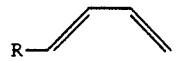

(II)

and maleic anhydride by Diels-Alder addition.

8 Claims, No Drawings

METHOD FOR THE CHEMICAL MODIFICATION OF PROTEINS

BACKGROUND OF THE INVENTION (1) Field of the Invention

This invention relates to a process for the chemical modification of proteins.

The chemical modification of proteins serves two major concerns It permits understanding of the structure and function of proteins as well as changes in these properties. These two aspects, knowledge of the structure and, in particular, of the active sites and changes in their activity, are particularly important in the case of proteins with a catalytic action such as enzymes.

(2) Background Art

The techniques for modifying proteins and the proteinaceous parts of enzymes are very varied:

It is possible to modify one or more amino acid residues specifically at the level of the active site of an enzyme for the purpose of studying (DS. SIGMAN Annu. Rev. Biochem 1975, 44, 899) or modifying (E. T. KAISER Annu. Rev Biochem. 1985, 54, 565) the catalytic activity. Suicide substrates may be classified in this category (WALSH Annu. Rev. Biochem 1984, 53, 493).

A single type of amino acid residue can be modified by a specific reagent. This method, which is described in the book "Chemical reagents for protein modification" (R. L. LUNDBLAD CRC Press, Bacaratan, USA, 1984) enable information to be obtained on the role of the type of residue affected.

Use of reagents which modify the protein for the purpose of its immobilization on a support, for example grafting of acryloyl groups followed by copolymerisation (K. MARTINER Biochem. Biophys. Acta 1977, 485 1) or the preparation of antibody-enzyme conjugates (D. M. BOORSMA J. Immunol Methods 1979, 30, 245)

Preparation of antigens by covalent binding of a small molecule to a protein (K. FLURKEY J. Neuroimmunol. 1985, 8 115).

Preparation of synthetic glycoproteins called neoglycoproteins (C. P. STOWELL Adv. Carb. Chem. Biochem 1980, 37 225).

Alteration of physicochemical properties such as stability or solubility in water or in organic solvents, by random reactions with the various active sites (V. V. MOZHAEV Aur. J. Biochem. 1988, 173 147).

We have now found a new method for the chemical modification of proteins which is very versatile and which permits the introduction of widely differing groups, both for the study of proteins and for the modification of their properties.

This method enables not only free amine groups to be attacked, but also the other protein functional groups with a nucleophilic character such as hydroxyl, thiol, thioether, imidazole or guanidine functional groups.

Another advantage of the method is the possibility of working either in an aqueous medium or in an organic medium depending on the site which it is desired to modify.

SUMMARY OF THE INVENTION

For this purpose, the method for the chemical modification of proteins, according to the invention, is characterized in that the protein is brought into contact, in a liquid medium, with a reagent of general formula:

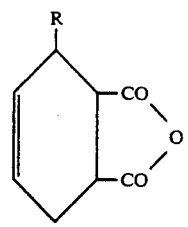

where R is a monovalent organic radical.

The organic radical R may be directly attached to the ring by a carbon-carbon bond or through a carbon-heteroatom bond, such as a carbon-oxygen, carbon-nitrogen or carbon-sulphur bond.

The nature of the organic radical R determines the direction of the modification. The choice is very wide, ranging from stabilization to hydrophilization by introduction of monosaccharides and to lipophilization by introduction of fatty chains.

The anhydride group of the reagent (I) reacts with the nucleophilic (Nu) residues of proteins, such as amine, hydroxyl, thiol, imidazole or guanidine groups:

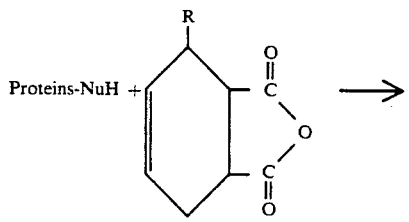

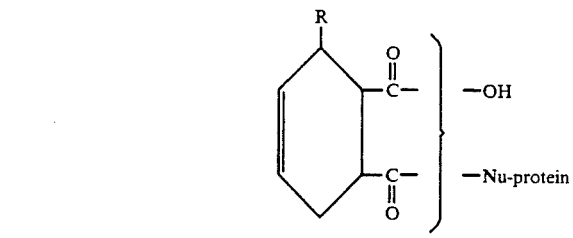

The reaction produces a new carboxylic functional group, which may be used in turn for introducing reagents and thus increasing the desired effect It is for example possible to form amides using a soluble carbodiimide.

It is evident that the chemical modification of a protein should be carried out under fairly mild conditions in order to preserve the structure and the activity of the protein.

DESCRIPTION OF THE PREFERRED EMBODIMENTS

The factors which play a major role in the protein deactivation process are the temperature, the ionic strength, the pH and the nature of the solvent. The high reactivity of the compound (I) enables the reaction to be carried out at low temperatures, if necessary between 5° and 10° C. The pH and the solvent are chosen so as to promote the reaction under consideration and to cause minimum denaturation of the protein. A compromise should be found for each protein and for each reaction.

The choice of solvent may also influence the nature of the nucleophilic groups which are attacked by the reagent. In an aqueous medium, the anhydride reacts especially with the free amine groups. Some organic solvents promote, in addition, the attack of the hydroxyl groups whereas the reactivity of the amine groups decreases in an organic solvent medium.

It can be assumed that the conformation of the protein is not the same in an aqueous solution as in suspension in an organic solvent.

Some amine groups are perhaps inaccessible or ionised, and therefore nonreactive, in these solvents.

The choice of solvent may represent an additional means of controlling the chemical conversion of a protein.

The reagent (I) may be easily prepared by Diels-Alder reaction of maleic anhydride and a diene of general formula:

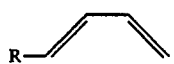

(II)

where R has the meaning given above.

The synthesis of the diene and its Diels-Alder addition to maleic anhydride are performed under mild conditions. It thus becomes possible to introduce very diverse R groups into the protein. The direct introduction of these R radicals onto an anhydride would often not be possible.

The Diels-Alder reaction is performed in an organic solvent.

Maleic anhydride, being the most reactive dienophile, promotes the reaction and enables it to be performed under mild conditions If the diene used is activated by the presence of electron-donating groups, the cycloaddition reaction will proceed even at room temperature.

The synthesis of the diene (II) depends of course on the nature of the organic radical R. We shall describe, by way of example, the synthesis of a diene containing a molecule of glucose and that of a diene containing fatty acid esters. These two examples demonstrate the great versatility of the method, which enables both hydrophilic and lipophilic groups to be introduced.

The synthesis of the diene where R is a glucose molecule is described by A. LUBINEAU (J. Org. Chem. 52, 1987 1001). This synthesis comprises the reaction of acetobromoglucose with the sodium salt of malonaldehyde and then with methylidene triphenylphosphorane. The diene obtained reacts in the form of the trimethylsilyl derivative with maleic anhydride to give the reagent (I) where R is a persilylated glucose molecule.

Reaction with a protein permits the synthesis of neoglucoproteins containing a large number of glucose molecules and therefore with a substantially increased hydrophilic character.

The glucose-containing reagent (I) may be used for the modification of proteins both in an aqueous medium and in an organic medium. It was used, by way of example, for modifying two proteins, bovine serum albumin (BSA) and a commonly used enzyme, horseradish peroxydase (HRP), in an aqueous or organic medium.

In an aqueous medium, the protein is dissolved in a pH 8 buffer of sufficient ionic strength. The reagent which is insoluble in the medium is added in small portions. The reaction is monitored by assaying the residual free amine functional groups of the protein. The hydroxyl functional groups of the sugars are regenerated by spontaneous hydrolysis of the silyl groups in the aqueous medium. After reisolating the protein, it is subjected to an assay of the free amine functional groups, and then after acid hydrolysis the bound glucose is assayed specifically, using a conventional enzymatic method.

In the case of BSA, the treatment led to the disappearance of all the titratable free amine functional groups, which corresponds to about twenty amine groups, and permits the binding of 80 glucose molecules per molecule of protein.

As BSA contains only 66 lysines, and therefore 66 amine groups, other residues were effected by reaction with (I), involving SH, OH, imidazole of guanidine functional groups.

In the case of HRP, the treatment leads to the disappearance of all the free amine functional groups (5.5) and permits the binding of 4 molecules of glucose per molecule of enzyme. 100% of the specific activity of the enzyme is recovered.

It is also possible to carry out the reaction in an organic medium. The choice of solvent depends on the nature of the enzyme to be treated.

The usual solvents for acylation reactions, such as pyridine, tetrahydrofuran or dimethylformamide, may for example be used. It happens that the best solvents for acylation reactions, such as pyridine and dimethylformamide, are also the most denaturing for proteins.

They may be used, however, for sufficiently robust proteins.

In the case of HRP, a mixture of tetrahydrofuran and pyridine is an acceptable compromise. In this case, the reagent is soluble in the medium and the protein, which is insoluble, remains in suspension. The silyl groups are hydrolysed once the reaction is completed After reisolating the protein, the free amine functional groups and the bound sugars are assayed. The treatment leaves two residual amine functional groups remaining out of the existing six and enables twenty molecules of glucose to be bound per molecule of enzyme. 20% of the specific activity is recovered.

The reaction in an organic medium thus permitted the binding of twenty molecules of glucose per molecule of enzyme, as against 3–4 in the aqueous phase. The number of glucose units bound increases linearly with the proportion of pyridine.

On the other hand, the specific activity also decreases linearly at the same time. A compromise should therefore be found for each enzyme and an optimisation is required.

The treatment with the reagent (I) produces one new carboxylic functional group per residue of glucose bound. These new carboxylic functional groups may be used for binding for example amine-containing compounds using a soluble carbodiimide. Glucosylamine was thus bound to BSA according to the method described by MOCZAR and VASS (Carboydr. Res. 1976 50 133). Acid hydrolysis of this product demonstrates the presence of 105 molecules of glucose per molecule of protein.

The glucosylamine treatment of the BSA itself enables only 4 to 5 glucosylamines to be bound to the 100 carboxylic acid functional groups which the protein contains.

Another example of chemical modification of proteins by the method according to the invention is the introduction of fatty acid chains in order to render the protein lipophilic.

The reagent is prepared by reaction of glyceric dimethylketal with allylidene triphenyl phosphorane.

After hydrolysis of the ketal, the diol obtained is esterified with stearyl chloride.

The diene reacts with maleic anhydride to give the reagent (I) where

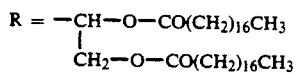

This compound was used to modify BSA and superoxide dismutase (SOD). The reaction is performed in an aqueous medium. After isolating the protein, the residual free amines are assayed, and then after alkali hydrolysis, the number of stearic acid molecules bound is determined by HPLC.

The first effect of the treatment on BSA is to render the protein insoluble in water, thereby preventing the assay of the free amine functional groups. The alkali hydrolysis releases 140 molecules of stearate per molecule of protein, corresponding to 70 molecules of reagent (I) bound.

The same treatment on SOD destroys all the titratable amine functional groups. The residual specific activity is 15%.

It is of course understood that these two examples, which are described in greater detail in the experimental section, do not in any way limit the scope of the invention.

EXAMPLES

Protein assay: by the bicinchoninic acid method (P. K. Smith Anal. Biochem. 1985 150 75) and/or by measuring the absorbance at 276 nm. The difference between the two methods does not exceed 10%.

Assay of free $NH_2$ functional groups: by the trinitrophenylsulphonic acid method (R. Field Biochem. J. 1972 124 581).

Assay of the bound glucose: 1 to 3 mg of purified, modified protein are hydrolysed with 1 ml of 2 M HCl for one hour at 100° C. in a screwtop tube closed after purging oxygen by flushing with nitrogen.

The acid is neutralised by passage through a Dowex 1-x 8 (mesh: 200), in formate form (2 ml). The glucose contained in the eluate is assayed by the hexokinase/glucose-6-phosphate dehydrogenase method (Methods in Carbohydrate Chem. III 135 (1980)).

EXAMPLE A

Synthesis of the diene A; I,R=silylated glucose

A.1. The diene:glucose —O—CH=CH—CH=CH$_2$ was prepared from acetobromoglucose by the method described by A. LUBINEAU (J. Org. Chem. 1987 52 1001).

The reaction of acetobromoglucose in dimethyl sulphoxide with the sodium salt of malonaldehyde gives 56% of an unsaturated aldehyde. The addition of methylenetriphenylphosphorane to this aldehyde at −78° C. in an oxolanetoluene mixture gives 83% of the diene derivative of glucose in the beta configuration.

The same reaction at room temperature gives 72% of the diene derivative in the alpha configuration. The diene (I), R=glucose, is obtained after deacetylation with a 1:8:1 triethylamine, methanol and water mixture with a practically quantitative yield.

A.2. The diene of Example A.1 is dissolved in 3 ml of anhydrous pyridine. 5.1 ml (24 mmol) of hexamethyldisilazane (HMDS) are added followed by 0.3 ml (3.9 mmol) of trifluoroacetic acid. After 6 hours at room temperature, the mixture is evaporated and then the product is distilled in a bulbed tube.

Yield=1.45 g (93%); b.p.$_{0.1\ mm}$=130°-140° C.; colourless liquid $[\alpha]_D^{20}$= −5.80° (C 1.2, CH$_2$Cl$_2$)

Elemental analysis: for $C_{22}H_{48}O_6Si_4$, Calculated: C 50.72%; H 9.29%. Found: C 50.90%; H 9.07%.

A.3. 274 mg (2.8 mmol) of freshly distilled maleic anhydride are added to 1.45 g (2.8 mmol) of the silylated diene of Example A.2 in solution in 1.8 ml of anhydrous THF.

After 12 hours at 40° C., the reaction is stopped and the volume is adjusted with anhydrous THF so as to obtain a 0.8 M solution which will be used as it is. This product is a mixture of three stereoisomers.

EXAMPLE B

Synthesis of the diene B;

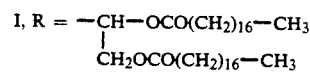

B.1.—Preparation of the diene HO—CH$_2$—CH(OH)—CH=CH—CH=CH$_2$ according to A. LUBINEAU et al., J. Chem. Soc. Perkin trans. 1 3011 (1990).

The glyceric aldehyde dimethylketal (8.55 g, 66 mmol) is added at −78° C. to a solution of allylidene phosphorane (66 mmol) in THF (350 ml) to give 72% of the protected diene in the form of a cis-trans mixture. The cis diene not being reactive in the Diels-Alder reaction, it can be quantitatively isomerised to the trans diene by reacting with a catalytic amount of iodine. Finally, the ketal is hydrolysed through contact with a DOWEX 50H$^+$ resin in an EtOH—H$_2$O (9:1) mixture.

(alpha)$_D^{20}$= −43° (c 1.8, EtOH)

Elemental analysis: for $C_6H_{10}O_2$, Calc.: C, 63.36: H, 8.83: O, 28.03. Found: C, 63.19: H, 8.30: O, 27.94.

B.2.—470 mg of the diene prepared according to B.1 are dissolved in 10 ml of anhydrous pyridine: 3 ml of stearoyl chloride are added dropwise (10.4 mmol). After 2 hours, the mixture is diluted with 100 ml of dichloromethane. The organic phase is washed with dilute hydrochloric acid, dried and then the solvent is evaporated. The product is purified by flash chromatography (100 ml of silica; toluene).

Amorphous solid (white paraffin);

Yield: 2.19 g (78%); m.p.=41°-49° C.; (alpha)$_D^{20}$= +9.3° C. (c=1.73; CH$_2$Cl$_2$)

Elemental analysis: for $C_{42}H_{78}O_4$, Calculated: C, 77.96%; H, 12.15%; O, 9.80%. Found: C, 77.97%; H, 12.24%) 9.99%.

B.3—1.61 g of the stearyl-containing diene of Example B.2 and 243 mg of freshly distilled maleic anhydride were dissolved in 0.5 ml. of anhydrous THF. After 24 hours at 70° C., the volume is adjusted with anhydrous THF so as to obtain a 0.75 M solution of the stearyl-containing compound I which will be used as it is.

1:1 mixture of two stereoisomers:

The melting point and the specific rotation are not determined since this is a mixture of stereoisomers.

Elemental analysis: for $C_{46}H_{80}O_7$ Calculated: C, 74.15%; H, 10.82%; O 15.03%. Found: C, 74.38%; H, 10.80%; O, 14.82%.

EXAMPLE 1

Modification of BSA (using A) in an aqueous medium 5 mg of BSA (5 micromol of $NH_2$) are dissolved in 3 ml of 0.07 M phosphate buffer pH 8. 400 microliters of a 0.8 M solution of A in THF (0.32 nmol) are added in fractions of 100 microliters at intervals of 1 hour. The reaction is performed with stirring on a rotary shaker. After 18 hours at 7° C., the pH is lowered to 3 to accelerate the hydrolysis of the silyls (the modified BSA precipitates). After 12 hours, the pH is adjusted to 7 (BSA redissolves) and the solution is extracted with 1 ml of dichloromethane. The protein is purified by passage through a Sephadex G50 column (50×2, 1 cm; eluent:0.02 M phosphate buffer pH 7; 0.5 ml/min.).

The fractions containing the protein are dialyzed against distilled water and then lyophilized. About 80–90% of the protein used was reversed. 80 molecules of A were bound per molecule of protein.

EXAMPLE 2

Modification of HRP using A in an aqueous medium 12 mg of HRP (0.28 micromole of $NH_2$ functional group) are dissolved in 2 ml of 0.07 M phosphate buffer pH 8.0, containing 0.1% of phenol. 0.5 ml of acetone is added followed by 200 microliters of anhydride solution in four fractions of 50 microliters at intervals of 1 hour. The experiment is therafter conducted as for BSA. About 60% of the protein used is recovered. 4 molecules of A were bound per molecule of protein.

EXAMPLE 3

Modification of HRP using A in organic solvent 1 ml of a 0.8 M solution of A in THF and 1 ml of a 60:40 THF:pyridine mixture are added to 50 mg of freeze-dried HRP.

The suspension is vigorously stirred for 48 hours at 37° C. on a rotary shaker. 18 ml of 0.07 M phosphate buffer pH 7 containing 0.1% of phenol are then added. After 4 hours at 7° C., the pH is reduced to 3 by addition of 6 M HCl (so as to accelerate the hydrolysis of the silyl groups).

After 2 hours at 7° C., the protein is separated from the organic solvents by passage through a Sephadex G-25 medium (21×3 cm; elution: 0.02 M phosphate buffer, pH 7). Three equivalents of hemin are added to the protein solution. After 18 hours at 4° C., the solution is freeze-dried and the residue taken up in 5 ml of double distilled water. The modified enzyme is purified by passage through Sephadex G-50 as described above. About 80% of the protein used is recovered. 20 molecules of A were bound per molecule of enzyme.

EXAMPLE 4

Modification of BSA using B in aqueous medium 4 mg of BSA ($6 \times 10^{-2}$ mmol of $NH_2$ functional group) are dissolved in 1 ml of 0.5 M phosphate buffer pH 8-THF (80:20). 120 microliters of a 0.57 M solution of B in THF are added in four fractions, at intervals of one hour, while the solution is being subjected to vigorous magnetic stirring. The reaction is allowed to proceed at 7° C. for 18 hours. The modified protein precipitates. It is centrifuged for 30 minutes at 0° C. and rinsed twice with 0.5 ml of a 20:80 THF : water mixture. 70 molecules of B were bound per molecule of protein.

EXAMPLE 5

Coupling of glucosylamine to A-modified BSA 6.6 mg BSA are dissolved in 0.15 ml of water. 22 mg of glucosylamine synthesised according to M. C. A. LOBRY de BRUYN (Rec. Trav. Chim. Pays-Bas 1985 12 98) are added and the pH is adjusted to 4–5 by addition of phosphoric acid. 30 mg of EDC are added in five portions over 1 hour and then another 22 mg of glucosylamine while maintaining the pH at 4–5.

The mixture is left stirring at 7° C for 15 hours and then the reaction is stopped by the addition of 30 ml of acetic acid. The protein is purified by chromatography on Sephadex PD 10, elution: 0.05 M acetate buffer pH 4.6. 25 molecules of glucosylamine were bound onto the modified BSA, which corresponds to 105 molecules of glucose per molecule of protein

We claim:

1. Method for the chemical modification of proteins, which comprises contacting a protein with a reagent of the formula:

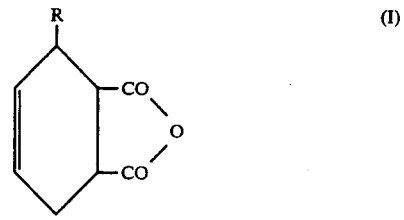

where R is a monovalent organic radical selected from the group consisting of monosaccharides and fatty acid chains.

2. Method according to claim 1, wherein the protein is brought into contact with the reagent (I) in an aqueous medium.

3. Method according to claim 1, wherein the protein is brought into contact with the reagent (I) in an organic solvent.

4. Method according to claim 3, wherein the organic solvent is pyridine, tetrahydrofuran, dimethylformamide or mixtures thereof.

5. Method according to claim 1 wherein the temperature is between 5° and 10° C.

6. Method according to claim 1 wherein the reagent of general formula (I) is prepared by Diels-Alder addition of a diene of general formula

where R has the meaning given above, onto maleic anhydride.

7. Method according to claim 1 wherein R is a glucose molecule.

8. Method according to claim 1 wherein R is a distearylglycol radical.

* * * * *